United States Patent
Lee et al.

(10) Patent No.: US 11,553,845 B2
(45) Date of Patent: Jan. 17, 2023

(54) BLOOD PRESSURE MEASURING APPARATUS AND BLOOD PRESSURE MEASURING METHOD

(71) Applicant: SAMSUNG ELECTRONICS CO., LTD., Suwon-si (KR)

(72) Inventors: Jong Wook Lee, Suwon-si (KR); Byung Hoon Ko, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 510 days.

(21) Appl. No.: 16/573,471

(22) Filed: Sep. 17, 2019

(65) Prior Publication Data
US 2020/0085323 A1 Mar. 19, 2020

(30) Foreign Application Priority Data
Sep. 18, 2018 (KR) .................. 10-2018-0111193

(51) Int. Cl.
*A61B 5/021* (2006.01)
*A61B 5/024* (2006.01)
*A61B 5/00* (2006.01)

(52) U.S. Cl.
CPC ...... *A61B 5/02108* (2013.01); *A61B 5/02433* (2013.01); *A61B 5/6843* (2013.01); *A61B 5/7278* (2013.01); *A61B 2562/0238* (2013.01)

(58) Field of Classification Search
None
See application file for complete search history.

(56) References Cited

U.S. PATENT DOCUMENTS

| | | |
|---|---|---|
| 9,795,309 B2 | 10/2017 | Shim et al. |
| 2014/0249763 A1 | 9/2014 | Shimuta |
| 2015/0359436 A1 | 12/2015 | Shim et al. |
| 2017/0079535 A1 | 3/2017 | Tchertkov et al. |
| 2017/0095168 A1 | 4/2017 | Kwon et al. |
| 2017/0143210 A1* | 5/2017 | Ikebe ............... A61B 5/02416 |

(Continued)

FOREIGN PATENT DOCUMENTS

| | | |
|---|---|---|
| JP | 2009-066042 A | 4/2009 |
| JP | WO2013054477 A1 | 4/2013 |

(Continued)

OTHER PUBLICATIONS

Anand Chandrasekhar, et al., "Smartphone-based blood pressure monitoring via the oscillometric finger-pressing method", Science Translational Medicine, Mar. 7, 2018, pp. 1-11 (12 pages total).

*Primary Examiner* — Yi-Shan Yang

(57) ABSTRACT

An apparatus for measuring blood pressure includes: a pulse wave measurer including a first light source configured to emit a first light, a second light source configured to emit a second light, and a photodetector configured to measure a pulse wave signal of an object based on the first light emitted by the first light source onto the object and returning from the object; a force measurer configured to measure a contact force between the object and the pulse wave measurer; and a processor configured to control emission of the second light from the second light source based on the measured contact force, and configured to estimate blood pressure of the object based on the measured pulse wave signal and the measured contact force.

17 Claims, 6 Drawing Sheets

(56) References Cited

U.S. PATENT DOCUMENTS

2017/0185737 A1    6/2017  Kovacs
2017/0251935 A1    9/2017  Yuen
2021/0244297 A1*   8/2021  Asvadi ................. A61B 5/0075

FOREIGN PATENT DOCUMENTS

| KR | 10-2005-0103354 A | 10/2005 |
| KR | 10-2015-0142310 A | 12/2015 |
| KR | 10-2016-0008129 A | 1/2016 |
| KR | 10-2017-0040034 A | 4/2017 |
| KR | 10-2017-0053019 A | 5/2017 |
| KR | 10-2018-0027299 A | 3/2018 |

* cited by examiner

BLOOD PRESSURE MEASURING APPARATUS AND BLOOD PRESSURE MEASURING METHOD

ROSS-REFERENCE TO RELATED APPLICATION(S)

This application claims priority from Korean Patent Application No. 10-2018-0111193, filed on Sep. 18, 2018, in the Korean Intellectual Property Office, the entire disclosure of which is herein incorporated by reference for all purposes.

BACKGROUND

1. Field

Example embodiments of the present disclosure relate to technology for cufflessly measuring blood pressure.

2. Description of Related Art

A pressurized cuff is generally used for measuring blood pressure. A blood pressure measuring method utilizing the pressurized cuff is a non-continuous measurement, in which the cuff is inflated until the arterial pressure reaches a maximum value, and then the pressure in the cuff is slowly released. However, the pressurized cuff includes a pressure pump and the like, such that the cuff is unsuitable for use in a mobile device.

Recently, research has been conducted on blood pressure measuring apparatuses for cufflessly measuring blood pressure in a non-pressure manner without using a cuff (that is, without applying pressure by using a cuff), and examples thereof include a blood pressure measuring apparatus using Pulse Transit Time (PTT) and a blood pressure measuring apparatus using Pulse Wave Analysis (PWA). However, the blood pressure measuring apparatus using PTT is inconvenient in that correction is required for each user to ensure accuracy of measurement; and since bio-signals should be measured at two or more positions to measure the pulse wave velocity, the apparatus cannot be manufactured in a compact size. Further, the blood pressure measuring apparatus using PWA estimates blood pressure by analyzing only a pulse wave form, such that the PWA is vulnerable to noise, and blood pressure may not be accurately measured.

SUMMARY

One or more example embodiments provide an apparatus and a method for cufflessly measuring blood pressure in which blood pressure may be measured with improved accuracy, and provide a compact size of the apparatus.

In an aspect of an example embodiment, there is provided an apparatus for measuring blood pressure includes: a pulse wave measurer including a first light source configured to emit a first light, a second light source configured to emit a second light, and a photodetector configured to measure a pulse wave signal of an object based on the first light emitted by the first light source onto the object and returning from the object; a force measurer configured to measure a contact force between the object and the pulse wave measurer; and a processor configured to control emission of the second light from the second light source based on the measured contact force, and configured to estimate a blood pressure of the object based on the measured pulse wave signal and the measured contact force.

The first light may be an infrared light, and the second light may be a light of a green wavelength or a red wavelength.

The processor may be configured to compare the measured contact force with a target force, and control at least one of an amount of the second light and a blinking speed of the second light source based on a result of the comparison.

The processor may be configured to compare the measured contact force with the target force that linearly increases over time.

The processor may be configured to decrease the amount of the second light based on the measured contact force being less than the target force, and configured to increase the amount of the second light based on the measured contact force being greater than the target force, or the processor may be configured to increase the amount of the second light based on the measured contact force being less than the target force, and configured to decrease the amount of the second light based on the measured contact force being greater than the target force.

The processor may be configured to decrease the blinking speed of the second light source based on the measured contact force being less than the target force, and configured to increase the blinking speed of the second light source based on the measured contact force being greater than the target force, or the processor may be configured to increase the blinking speed of the second light source based on the measured contact force being less than the target force, and configured to decrease the blinking speed of the second light source based on the measured contact force being greater than the target force.

The processor may be configured to decrease the amount of the second light based on the measured contact force being less than the target force, and the processor may be configured to decrease the blinking speed of the second light source based on the measured contact force being greater than the target force, or the processor may be configured to decrease the blinking speed of the second light source based on the measured contact force being less than the target force, and the processor may be configured to decrease the amount of the second light based on the measured contact force being greater than the target force.

The processor may be configured to decrease the amount of the second light based on the measured contact force being less than the target force, and configured to increase the blinking speed of the second light source based on the measured contact force being greater than the target force, or based on the measured contact force being less than the target force, the processor may be configured to increase the blinking speed of the second light source, and based on the measured contact force being greater than the target force, the processor may be configured to decrease the amount of the second light.

The processor may be configured to increase the amount of the second light based on the measured contact force being less than the target force, and configured to decrease the blinking speed of the second light source based on the measured contact force being greater than the target force, or the processor may be configured to decrease the blinking speed of the second light source based on the measured contact force being less than the target force, and configured to increase the amount of the second light based on the measured contact force being greater than the target force.

The processor may be configured to increase the amount of the second light based on the measured contact force being less than the target force, and configured to increase the blinking speed of the second light source based on the measured contact force being greater than the target force, or the processor may be configured to increase the blinking speed of the second light source based on the measured contact force being less than the target force, and configured to increase the amount of the second light based on the measured contact force being greater than the target force.

Based on the measured contact force, the processor may be configured to, based on the measured contact force, determine a contact pressure between the object and the pulse wave measurer, and estimate the blood pressure of the object based on the determined contact pressure and the measured pulse wave signal.

The apparatus may further include an output part configured to output an estimation result of the blood pressure.

In an aspect of an example embodiment, there is provided a method for measuring blood pressure, the method including: measuring, by using a pulse wave measurer, a pulse wave signal of an object based on a first light emitted by a first light source onto the object and returning from the object; measuring a contact force between the object and the pulse wave measurer; controlling emission of a second light from a second light source based on the measured contact force; and estimating a blood pressure of the object based on the measured pulse wave signal and the measured contact force.

The first light may be an infrared light, and the second light may be a light of a green wavelength or a red wavelength.

The controlling may include comparing the measured contact force with a target force; and controlling at least one of an amount of the second light and a blinking speed of the second light source based on a result of the comparing.

The comparing may include comparing the measured contact force with the target force that linearly increases over time.

The estimating may include based on the measured contact force, determining a contact pressure between the object and the pulse wave measurer; and estimating the blood pressure of the object based on the determined contact pressure and the measured pulse wave signal.

The method may further include outputting an estimation result of the blood pressure.

In an aspect of an example embodiment, there is provided an apparatus for measuring blood pressure, the apparatus including: a light source configured to emit light; a pulse wave measurer configured to measure a pulse wave signal of an object by using the light emitted by the light source; a force measurer configured to measure a contact force between the object and the pulse wave measurer; and a processor configured to control emission of the light by the light source based on the measured contact force, and configured to estimate blood pressure of the object based on the measured pulse wave signal and the measured contact force.

The light source may emit a visible light.

BRIEF DESCRIPTION OF THE DRAWINGS

The above and/or other aspects will become apparent and more readily appreciated from the following description of the embodiments, taken in conjunction with the accompanying drawing, in which.

DETAILED DESCRIPTION

Figure 1:
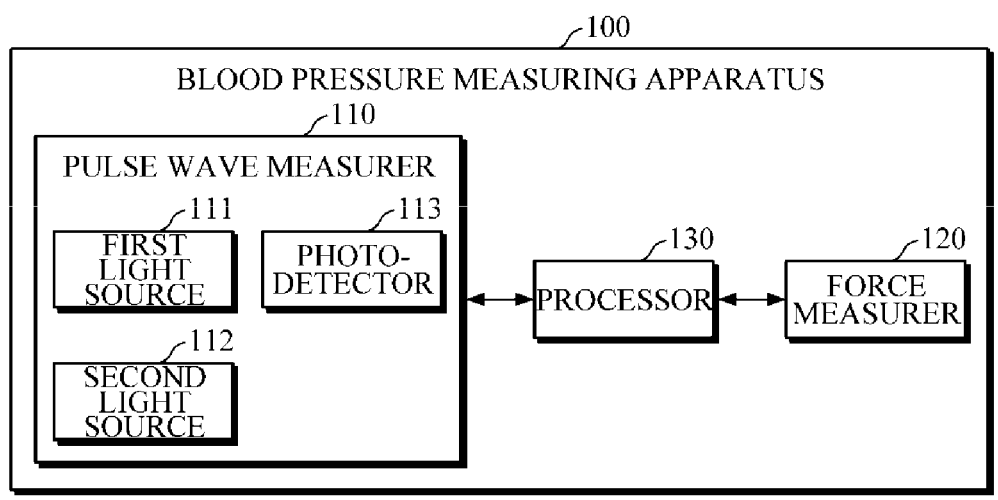
FIG. 1 is a block diagram illustrating an example of a blood pressure measuring apparatus according to an example embodiment.

Hereinafter, example embodiments will be described in detail with reference to the accompanying drawings. It should be noted that, in the drawings, the same reference symbols refer to same parts although illustrated in other drawings. Throughout the drawings and the detailed description, unless otherwise described, the same drawing reference numerals will be understood to refer to the same elements, features, and structures. The relative size and depiction of these elements may be exaggerated for clarity, illustration, and convenience. In the following description, a detailed description of known functions and configurations incorporated herein will be omitted when it may obscure the subject matter of the disclosure.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

In addition, the terms, such as 'part' or 'unit', etc., should be understood as a unit that performs at least one function or operation and that may be embodied as hardware, software, or a combination thereof.

Figure 2:
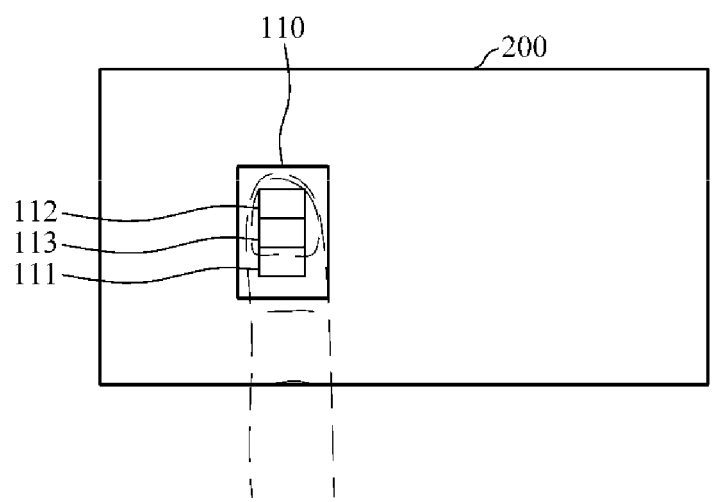
FIG. 2 is a diagram illustrating an example where a blood pressure measuring apparatus is provided in a mobile device according to an example embodiment.

FIG. 1 is a block diagram illustrating an example of a blood pressure measuring apparatus according to an example embodiment; and FIG. 2 is a diagram illustrating an example where a blood pressure measuring apparatus according to an example embodiment is provided in a mobile device.

The blood pressure measuring apparatus 100 of FIG. 1 is an apparatus for estimating blood pressure of an object based on a pulse wave signal. In this case, examples of the electronic devices may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 1, the blood pressure measuring apparatus 100 includes a pulse wave measurer 110, a force measurer 120, and a processor 130.

The pulse wave measurer 110 may measure a pulse wave signal of an object. Here, the object may be a distal body portion, such as a finger, a toe, an earlobe, and the like, and the pulse wave signal may be a photoplethysmogram signal. In one example embodiment, once an object touches the pulse wave measurer 110, the pulse wave measurer 110 may emit light of a predetermined wavelength onto the object, and may measure a pulse wave signal of the object by emitting light of a predetermined wavelength onto the object and receiving light returning from the object. The pulse wave measurer 110 includes a first light source 111, a second light source 112, and a photodetector 113.

The first light source 111 may be a light source used for measuring a pulse wave signal of an object. The first light source 111 may emit light of a predetermined wavelength (hereinafter referred to as first light) onto an object touching the pulse wave measurer 110. For example, the first light source 111 may emit infrared rays (IR) onto an object. However, wavelengths of the first light emitted by the first light source 111 may vary depending on the purpose of measurement or the types of target components to be analyzed. Further, the light source 111 may not be a single light-emitting body, and may be an array of a plurality of light-emitting bodies. In this case, each light emitting body may emit light of the same wavelength, or light of different wavelengths. The first light source 111 may include a light emitting diode (LED), a laser diode, a fluorescent body, or the like.

The second light source 112 may be a light source used for inducing a change in a contact force between an object and the pulse wave measurer 110. The second light source 112 may emit light of a predetermined wavelength (hereinafter referred to as second light) onto an object touching the pulse wave measurer 110. For example, the second light source 112 may emit light of a red wavelength or a green wavelength onto an object. Further, the second light source 112 may not be a single light-emitting body, and may be an array of a plurality of light-emitting bodies. In this case, each light emitting body may emit light of the same wavelength, or light of different wavelengths. The second light source 112 may include a light emitting diode (LED), a laser diode, a fluorescent body, or the like.

The first light source 111 and the second light source 112 may be driven in a time-division manner under the control of the processor 130. In this case, light source driving conditions, such as an emission time, a driving sequence, a current intensity, a pulse duration, and the like of the first light source 111 and the second light source 112, may be preset.

The photodetector 113 may measure a pulse wave signal of an object based on the first light, which is emitted by the first light source 111 and is reflected or scattered from the object. In one example embodiment, the photodetector 113 may include a photo diode, a photo transistor (PTr), a charge-coupled device (CCD), or the like. The photodetector 113 may not be a single device, but may be an array of a plurality of devices.

Referring to FIG. 2, in the case where the blood pressure measuring apparatus 100 is provided (or embedded) in a mobile device 200, the pulse wave measurer 110 may be disposed on a rear surface of the mobile device 200. In order to accurately estimate blood pressure of an object by using a contact force and a pulse wave signal of an object, an appropriate magnitude of a contact force should be applied between an object and the pulse wave measurer 110 over time, and it is required to measure a pulse wave signal having a signal-to-noise ratio (SNR) with no motion noise. Accordingly, there is a need to provide a user with information to guide the user such that an object pushes the pulse wave measurer 110 with an appropriate force, and the information may be generally provided on a display. However, the mobile device 200 generally has no display on the rear surface, such that it is not easy to apply an appropriate contact force between the object and the pulse wave measurer 110 without motion noise.

Accordingly, in the blood pressure measuring apparatus 100 according to an example embodiment of the disclosure, the pulse wave measurer 110 is disposed on a rear surface of the mobile device 200, and may measure a pulse wave signal using the first light source 111 and the photodetector 113 and guide (or induce) the user to increase or decrease a contact force between the object and the pulse wave measurer 110 by controlling an amount of light or a blinking speed of the second light source 112. In this case, the first light source 111 and the second light source 112 may be disposed adjacent to each other, so that when an object touches the pulse wave measurer 110 to measure a pulse wave signal, the object may be positioned above the first light source 111 and the second light source 112.

The force measurer 120 may measure a contact force between the object and the pulse wave measurer 110. To this end, the force measurer 120 may include a force sensor and the like. In one example embodiment, the force measurer 120 may be disposed below the pulse wave measurer 110.

The processor 130 may control the overall operation of the blood pressure measuring apparatus 100.

In response to an occurrence of a specific event such as a blood pressure measuring command and the like, the processor 130 may generate guidance information for measuring blood pressure of an object, and may provide the guidance information to a user through an output device. In this case, the guidance information may include information for guiding a user's action to touch the pulse wave measurer 110 with an object to measure a pulse wave signal of the object, and information indicating the meaning of a change in an amount of light or a blinking speed of the second light source 112. Further, the output device may include a visual output device (e.g., display), an acoustic output device (e.g., speaker), a tactile output device (e.g., vibrator), and the like.

Once an object touches the pulse wave measurer 110, the processor 130 may control the first light source 111 and the photodetector 113 to measure a pulse wave signal of the object, and may control the force measurer 120 to measure a contact force between the object and the pulse wave measurer 110.

Based on the contact force measured by the force measurer 120, the processor 130 may control the second light source 120 to guide (or induce) the user to increase or decrease the contract force between the object and the pulse wave measurer 110. For example, the processor 130 may compare the measured contact force with a desired contact force (hereinafter referred to as a target force), and may control an amount of light, a blinking speed, and the like of the second light source 112 based on the comparison result, so that a user may change the contact force. That is, by controlling an amount of light or a blinking speed of the second light source 112, the processor 130 may induce increase or decrease in the contact force between the object and the pulse wave measurer 110. In this case, the target force may linearly increase over time.

In one example embodiment, in response to the measured contact force being less than the target force, the processor 130 may decrease an amount of light of the second light source 112; and in response to the measured contact force being greater than the target force, the processor 130 may increase an amount of light of the second light source 112. On the other hand, alternatively, in response to the measured contact force being less than the target force, the processor 130 may increase an amount of light of the second light source 112; and in response to the measured contact force being greater than the target force, the processor 130 may decrease an amount of light of the second light source 112.

In another example embodiment, in response to the measured contact force being less than the target force, the processor 130 may decrease a blinking speed of the second light source 112; and in response to the measured contact force being greater than the target force, the processor 130 may increase a blinking speed of the second light source 112. On the other hand, alternatively, in response to the measured contact force being less than the target force, the processor 130 may increase a blinking speed of the second light source 112; and in response to the measured contact force being greater than the target force, the processor 130 may decrease a blinking speed of the second light source 112.

In yet another example embodiment, in response to the measured contact force being less than the target force, the processor 130 may decrease an amount of light of the second light source 112; and in response to the measured contact force being greater than the target force, the processor 130 may decrease a blinking speed of the second light source 112. On the other hand, alternatively, in response to the measured contact force being less than the target force, the processor 130 may decrease a blinking speed of the second light source 112; and in response to the measured contact force being greater than the target force, the processor 130 may decrease an amount of light of the second light source 112.

In still another example embodiment, in response to the measured contact force being less than the target force, the processor 130 may decrease an amount of light of the second light source 112; and in response to the measured contact force being greater than the target force, the processor 130 may increase a blinking speed of the second light source 112. On the other hand, alternatively, in response to the measured contact force being less than the target force, the processor 130 may increase a blinking speed of the second light source 112; and in response to the measured contact force being greater than the target force, the processor 130 may decrease an amount of light of the second light source 112.

In still another example embodiment, in response to the measured contact force being less than the target force, the processor 130 may increase an amount of light of the second light source 112; and in response to the measured contact force being greater than the target force, the processor 130 may decrease a blinking speed of the second light source 112. On the other hand, alternatively, in response to the measured contact force being less than the target force, the processor 130 may decrease a blinking speed of the second light source 112; and in response to the measured contact force being greater than the target force, the processor 130 may increase an amount of light of the second light source 112.

In yet another example embodiment, in response to the measured contact force being less than the target force, the processor 130 may increase an amount of light of the second light source 112; and in response to the measured contact force being greater than the target force, the processor 130 may increase a blinking speed of the second light source 112. On the other hand, alternatively, in response to the measured contact force being less than the target force, the processor 130 may increase a blinking speed of the second light source 112; and in response to the measured contact force being greater than the target force, the processor 130 may increase an amount of light of the second light source 112.

Once the amount of light or the blinking speed of the second light source 112 changes, a user may visually recognize the change in the amount of light or the blinking speed of the second light source 112 from the second light passing through an object, which allows the user to control the contact force (e.g., to increase or decrease the contact force) between the object and the pulse wave measurer 110.

Based on the contact force measured by the force measurer 120, the processor 130 may calculate contact pressure between the object and the pulse wave measurer 110. In one example embodiment, based on the contact force between the object and the pulse wave measurer 110 and a contact area therebetween, the processor 130 may measure contact pressure between the object and the pulse wave measurer 110. In this case, the contact area between the object and the pulse wave measurer 110 may be predetermined as a default and may be stored in an internal or external memory, or may be measured by using a separate contact area sensor.

Further, the processor 130 may estimate blood pressure of an object based on a pulse wave signal of the object, and contact pressure between the object and the pulse wave measurer 110. For example, the processor 130 may estimate a user's blood pressure by analyzing an amplitude change of a pulse wave signal according to a contact pressure change.

Blood pressure may include Diastolic Blood Pressure (DBP), Systolic Blood Pressure (SBP), and Mean Arterial Pressure (MAP); and the contact pressure applied to the object may act as an external pressure on blood vessels. In the case where the contact pressure is lower than the MAP, an elastic restoring force of tissues act to constrict the blood vessels, such that the amplitude of the pulse waves is reduced; in the case where the contact pressure is equal to the MAP, the elastic restoring force of tissues becomes zero, having no effect on the blood vessels, such that the amplitude of the pulse waves reaches its peak value. Further, in the case where the contact pressure is greater than the MAP, the elastic restoring force of tissues act to dilate the blood vessels, such that the amplitude of the pulse waves is reduced. Accordingly, by analyzing the amplitude change of the pulse wave signal according to the contact pressure, the processor 150 may estimate, as the MAP, a contact pressure value at a peak amplitude of the pulse wave signal. Further, the processor 130 may estimate, as the systolic blood pressure (SBP), a contact pressure value at a point where a ratio of an amplitude value to the peak amplitude is a first ratio (e.g., 0.6); and may estimate, as the diastolic blood pressure (DBP), a contact pressure at a point where a ratio of an amplitude value to the peak amplitude is a second ratio (e.g., 0.7).

Upon completing estimation of blood pressure, the processor 130 may provide the estimation result to a user through an output device. In this case, the output device may include a visual output device (e.g., display), an acoustic output device (e.g., speaker), a tactile output device (e.g., vibrator), and the like.

Figure 3:
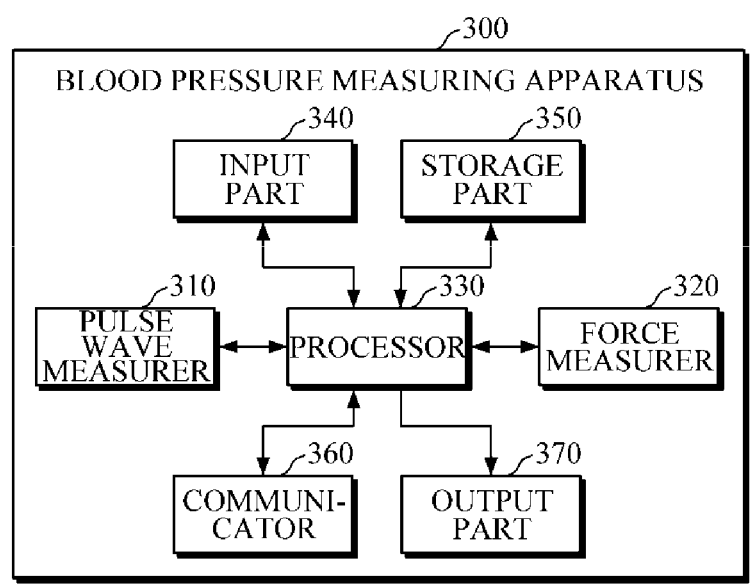
FIG. 3 is a block diagram illustrating another example of a blood pressure measuring apparatus according to an example embodiment.

FIG. 3 is a block diagram illustrating another example of a blood pressure measuring apparatus according to an example embodiment. The blood pressure measuring apparatus 300 of FIG. 3 may be provided (or embedded) in an electronic device. Examples of the electronic devices may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 3, the blood pressure measuring apparatus 300 includes a pulse wave measurer 310, a force measurer 320, a processor 330, an input part 340, a storage part 350, a communicator 360, and an output part 370. Here, the pulse wave measurer 310, the force measurer 320, and the processor 330 are the same as or similar to the pulse wave measurer 110, the force measurer 120, and the processor 130 of FIG. 1, such that detailed description thereof will be omitted.

The input part 340 may receive input of various operation signals from a user. In one example embodiment, the input part 340 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage part 350 may store programs or cot ands for operation of the blood pressure measuring apparatus 300, and may store data input to and output from the blood pressure measuring apparatus 300. Further, the storage part 350 may store data obtained or processed by the blood pressure measuring apparatus 300, and information to be used for processing data of the blood pressure measuring apparatus 300.

The storage part 350 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the blood pressure measuring apparatus 300 may operate an external storage medium, such as web storage and the like, which performs a storage function of the storage part 350 on the Internet.

The communicator 360 may perform communication with an external device. For example, the communicator 360 may transmit, to the external device, data input by a user through the input part 340, the data obtained or processed by the blood pressure measuring apparatus 300, and information to be used for processing data of the blood pressure measuring apparatus 300, and the like; or may receive, from the external device, various data useful for estimation of blood pressure.

In this case, the external device may be medical equipment using the data input by a user through the input part 340, the data obtained or processed by each of the blood pressure measuring apparatus 300, and the information to be used for processing data of the blood pressure measuring apparatus 300, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 360 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are merely examples and are not intended to be limiting.

The output part 370 may output the data input by a user through the input part 340, the data obtained or processed by the blood pressure measuring apparatus 300, and the information to be used for processing data of the blood pressure measuring apparatus 300, and the like. In one example embodiment, the output part 370 may output the data input by a user through the input part 340, the data obtained or processed by the blood pressure measuring apparatus 300, and the information to be used for processing data of the blood pressure measuring apparatus 300, and the like by using at least one of an acoustic method, a visual method, and a tactile method. To this end, the output part 370 may include a display, a speaker, a vibrator, and the like.

Figure 4:
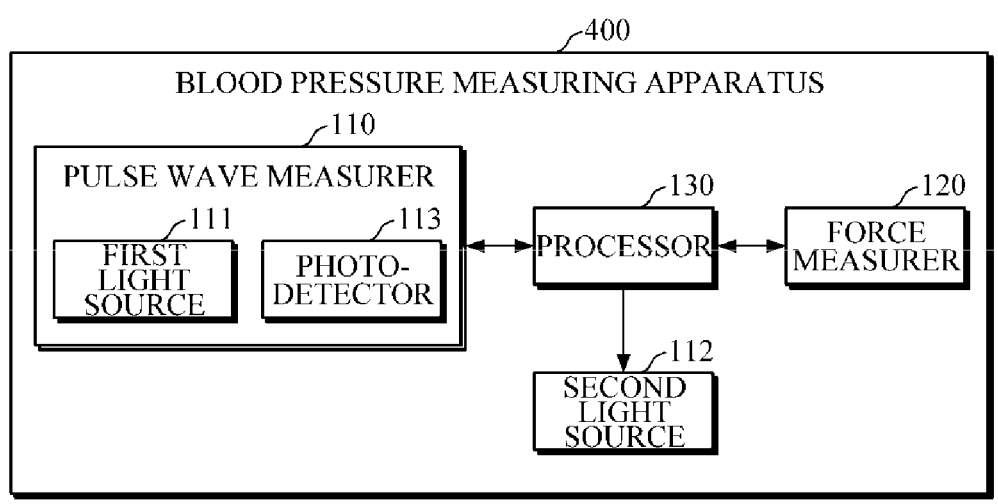
FIG. 4 is a block diagram illustrating yet another example of a blood pressure measuring apparatus according to an example embodiment.
Figure 5:
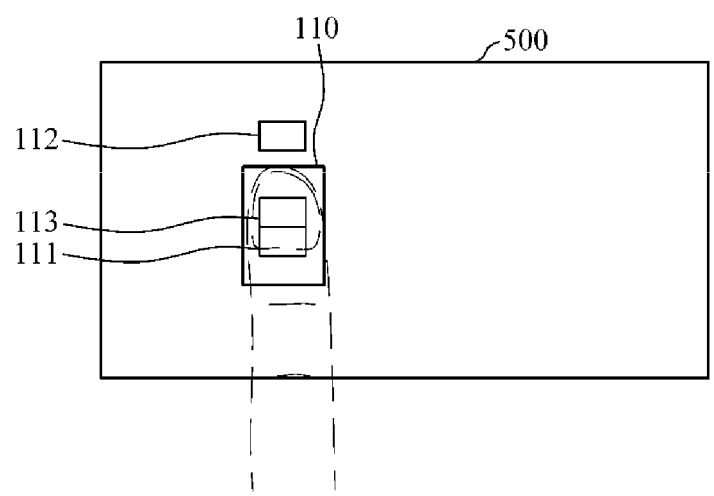
FIG. 5 is a diagram illustrating an example where a blood pressure measuring apparatus is provided in a mobile device according to an example embodiment.

FIG. 4 is a block diagram illustrating yet another example of a blood pressure measuring apparatus according to an example embodiment; and FIG. 5 is a diagram illustrating an example where a blood pressure measuring apparatus is provided in a mobile device according to an example embodiment.

Unlike the blood pressure measuring apparatus 100 of FIG. 1, the second light source 112 of the blood pressure measuring apparatus 400 of FIG. 4 is disposed on the outside of the pulse wave measurer 110. In this case, light emitted by the second light source 112 may be any light in a visible light range which is recognizable by a user.

Referring to FIG. 5, the second light source 112 may be disposed on a rear surface of the mobile device 500 on the outside of the pulse wave measurer 110. In this case, the second light source 112 may be spaced apart from the pulse wave measurer 110 by a predetermined distance, so that when an object touches the pulse wave measurer 110 to measure a pulse wave signal, the object is not positioned above the second light source 112. As the object is not positioned above the second light source 112 when a pulse wave signal is measured, the user may immediately recognize light emitted by the second light source 112. Accordingly, light emitted by the second light source 112 may be any light in a visible light range which is recognizable by a user.

Figure 6:
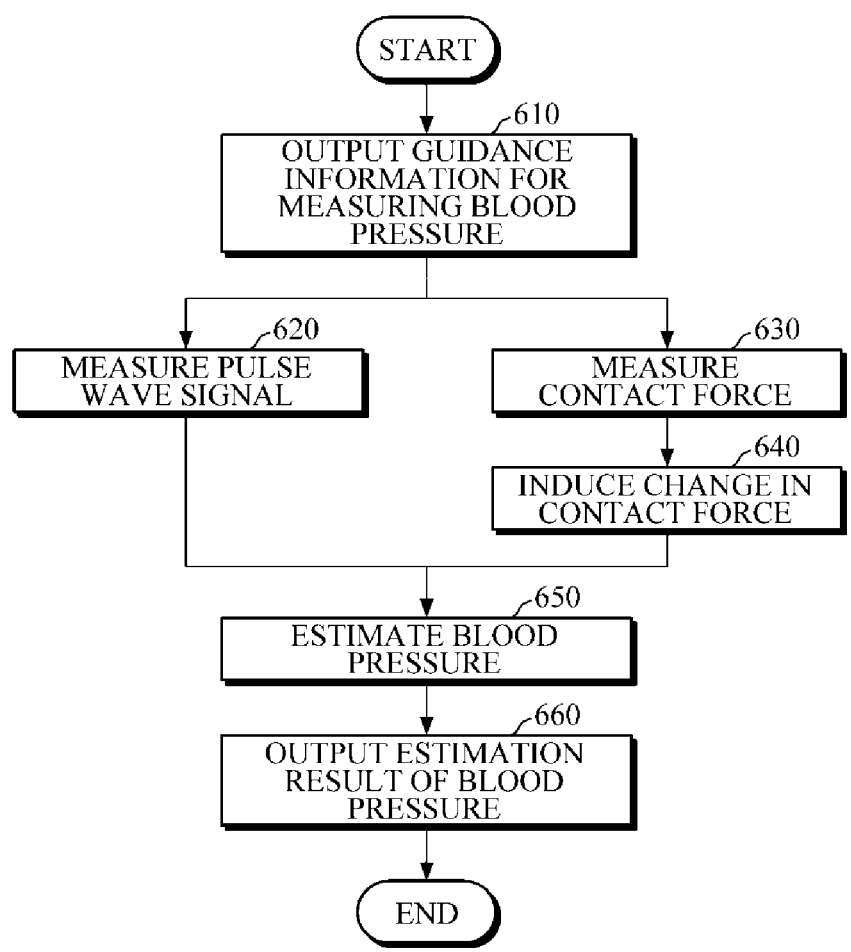
FIG. 6 is a flowchart illustrating an example of a blood pressure measuring method according to an example embodiment.

FIG. 6 is a flowchart illustrating an example of a blood pressure measuring method according to an example embodiment. The blood pressure measuring method of FIG. 6 may be performed by any one of the blood pressure measuring apparatuses 100, 300, and 400 of FIGS. 1, 3, and 4.

Referring to FIG. 6, in response to an occurrence of a specific command such as a blood pressure measuring command and the like, the blood pressure measuring apparatus may generate guidance information for measuring blood pressure of an object, and may provide the guidance information to a user through an output device, in 610. In this case, the guidance information may include information for inducing a user's action to touch the pulse wave measurer with an object to measure a pulse wave signal of the object, and information indicating the meaning of a change in an amount of light or a blinking speed of the second light source 112.

The blood pressure measuring apparatus may measure a pulse wave signal of an object, in 620. In this case, the pulse wave signal may be a photoplethysmogram signal. In one example embodiment, when an object touches the pulse wave measurer, the blood pressure measuring apparatus may emit light of a predetermined wavelength (e.g., infrared light) onto the object by using the first light source, and may measure a pulse wave signal of the object by receiving light returning from the object.

The blood pressure measuring apparatus may measure a contact force between the object and the pulse wave measurer, in 630.

Based on the measured contact force, the blood pressure measuring apparatus may control the second light source to induce increase or decrease in the contact force between the object and the pulse wave measurer, in 640. For example, the blood pressure measuring apparatus may compare the measured contact force with a desired contact force (target force), and may control an amount of light, a blinking speed, and the like of the second light source based on the comparison result, so that a user may change the contact force.

In this case, the second light source may be a light source emitting a visible light (e.g., light of a red wavelength or a green wavelength).

The blood pressure measuring g apparatus may estimate blood pressure of an object based on the measured contact force and the measured pulse wave signal, in 650. For example, the blood pressure measuring apparatus may calculate contact pressure between the object and the pulse wave measurer by using the measured contact force, and may measure blood pressure of the object by using the calculated contact pressure and the measured pulse wave signal.

Upon completing estimation of blood pressure, the blood pressure measuring apparatus may provide the estimation result to a user in 660. In this case, the output device may include a visual output device (e.g., display), an acoustic output device (e.g., speaker), a tactile output device (e.g., vibrator), and the like.

The example embodiments of the disclosure can be realized as a computer-readable code written on a computer-readable recording medium. The computer-readable recording medium may be any type of recording device in which data is stored in a computer-readable manner. Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed there decentralized manner. Functional programs, codes, and code segments needed for realizing the example embodiments of the disclosure can be easily deduced by one of ordinary skill in the art.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

Several example embodiments have been described above, but a person of ordinary skill in the art will understand and appreciate that various modifications can be made without departing the scope of the disclosure. Thus, it will be apparent to those ordinary skilled in the art that the true scope of technical protection is only defined by the following claims.

What is claimed is:

1. An apparatus for measuring a blood pressure, the apparatus comprising:
    a pulse wave measurer comprising:
        a first light source configured to emit a first light;
        a second light source configured to emit a second light; and
        a photodetector configured to measure a pulse wave signal of an object based on the first light emitted by the first light source onto the object and returning from the object;
    a force measurer configured to measure a first contact force and a second contact force between the object and the pulse wave measurer; and
    a processor configured to:
        control the emission of the second light from the second light source to guide the object to increase or decrease the first contact force based on at least one of an amount of the second light and a blinking speed of the second light source, wherein
            the emission of the second light is controlled such that at least one of the amount of the second light and the blinking speed of the second light source is changed differently depending on whether the first contact force is greater or less than a target force,
            the second contact force is measured after the object increases or decreases the first contact force, and
            the second contact force is more approximate to the target force than the first contact force, and
        estimate a blood pressure of the object based on the measured pulse wave signal and the second contact force.

2. The apparatus of claim 1, wherein the first light is an infrared light, and the second light is a light of a green wavelength or a red wavelength.

3. The apparatus of claim 1, wherein the processor is further configured to compare the first contact force with the target force that linearly increases over time.

4. The apparatus of claim 1, wherein:
    the processor is further configured to decrease the amount of the second light based on the first contact force being less than the target force, and to increase the amount of the second light based on the first contact force being greater than the target force, or
    the processor is further configured to increase the amount of the second light based on the first contact force being less than the target force, and to decrease the amount of the second light based on the first contact force being greater than the target force.

5. The apparatus of claim 1, wherein:
    the processor is further configured to decrease the blinking speed of the second light source based on the first contact force being less than the target force, and configured to increase the blinking speed of the second light source based on the first contact force being greater than the target force, or
    the processor is further configured to increase the blinking speed of the second light source based on the first contact force being less than the target force, and configured to decrease the blinking speed of the second light source based on the first contact force being greater than the target force.

6. The apparatus of claim 1, wherein:
    the processor is further configured to decrease the amount of the second light based on the first contact force being less than the target force, and the processor is configured to decrease the blinking speed of the second light source based on the first contact force being greater than the target force, or
    the processor is further configured to decrease the blinking speed of the second light source based on the first contact force being less than the target force, and the processor is configured to decrease the amount of the second light based on the first contact force being greater than the target force.

7. The apparatus of claim 1, wherein:
    the processor is further configured to decrease the amount of the second light based on the first contact force being less than the target force, and to increase the blinking speed of the second light source based on the first contact force being greater than the target force, or
    the processor is further configured to increase the blinking speed of the second light source based on the first contact force being less than the target force, and to decrease the amount of the second light based on the first contact force being greater than the target force.

8. The apparatus of claim 1, wherein:
    the processor is further configured to increase the amount of the second light based on the first contact force being less than the target force, and to decrease the blinking speed of the second light source based on the first contact force being greater than the target force, or
    the processor is further configured to decrease the blinking speed of the second light source based on the first contact force being less than the target force, and to increase the amount of the second light based on the first contact force being greater than the target force.

9. The apparatus of claim 1, wherein:
    the processor is further configured to increase the amount of the second light based on the first contact force being less than the target force, and to increase the blinking speed of the second light source based on the first contact force being greater than the target force, or
    the processor is further configured to increase the blinking speed of the second light source based on the first contact force being less than the target force, and to increase the amount of the second light based on the first contact force being greater than the target force.

10. The apparatus of claim 1, wherein the processor is further configured to, based on the second contact force, determine a contact pressure between the object and the pulse wave measurer, and estimate the blood pressure of the object based on the determined contact pressure and the pulse wave signal.

11. The apparatus of claim 1, further comprising an output circuit configured to output an estimation result of the blood pressure.

12. The apparatus of claim 1, wherein the second light source emits a visible light.

13. A method for measuring a blood pressure, the method comprising:
    emitting a first light from a first light source onto an object;

emitting a second light from a second light source;

measuring, by using a pulse wave measurer, a pulse wave signal of the object based on the first light emitted by the first light source onto the object and returning from the object;

measuring a first contact force and a second contact force between the object and the pulse wave measurer;

comparing the first contact force and a target force;

controlling the emission of the second light from the second light source to guide the object to increase or decrease the first contact force based on at least one of an amount of the second light and a blinking speed of the second light source, wherein the emission of the second light is controlled such that at least one of the amount of the second light and the blinking speed of the second light source is changed differently depending on whether the first contact force is greater or less than the target force, the second contact force is measured after the object increases or decreases the first contact force, and the second contact force is more approximate to the target force than the first contact force; and estimating a blood pressure of the object based on the pulse wave signal and the second contact force.

14. The method of claim 13, wherein the first light is an infrared light, and the second light is a light of a green wavelength or a red wavelength.

15. The method of claim 13, wherein the comparing comprises comparing the first contact force with the target force that linearly increases over time.

16. The method of claim 13, wherein the estimating comprises:

based on the second contact force, determining a contact pressure between the object and the pulse wave measurer; and estimating the blood pressure of the object based on the determined contact pressure and the pulse wave signal.

17. The method of claim 13, further comprising outputting an estimation result of the blood pressure.

* * * * *